United States Patent [19]

Edelman

[11] 4,187,609
[45] Feb. 12, 1980

[54] SUBMERGED FUNCTIONAL IMPLANT AND METHOD

[76] Inventor: Alfred E. Edelman, 2723 Federal St., Camden, N.J. 08105

[21] Appl. No.: 925,764

[22] Filed: Jul. 18, 1978

Related U.S. Application Data

[63] Continuation of Ser. No. 819,119, Jul. 26, 1977, abandoned, which is a continuation of Ser. No. 559,226, Mar. 17, 1975, abandoned.

[51] Int. Cl.² .............................................. A61C 13/00
[52] U.S. Cl. .................................................... 433/176
[58] Field of Search .......................... 32/10 A, 2, 8, 10

[56] References Cited

U.S. PATENT DOCUMENTS

| | | | |
|---|---|---|---|
| 3,589,011 | 6/1971 | Sneer | 32/10 A |
| 3,952,414 | 4/1976 | Shovers | 32/10 A |

FOREIGN PATENT DOCUMENTS 610723  11/1960  Italy .......................................... 32/10 A

*Primary Examiner*—Robert Peshock

[57] ABSTRACT

A suitable dental implant which I term a submerged dental implant and which may be of either the post or blade type, but preferably the latter is provided with a relatively short, hollow, threaded neck or collar portion to which a thin temporary cap may be detachably applied.

The implant including the neck with the cap applied, is then inserted in a cavity formed in the jawbone of the patient to a depth where the implant is entirely submerged. Thereafter, the mucosa (gum) is laid over the cavity completely covering the implant and a suture is applied. After a suitable period of time which may be in the order of several weeks or even months, as determined by tests by the doctor or surgeon in charge, the covering skin is removed from the cavity and the temporary cap is replaced by a tooth-receiving head member, a portion of which projects above the surface of the gum. An artificial tooth or other dental device is then applied to the head member. Suitable tools may be employed in applying the caps and the head member and in removing the caps.

1 Claim, 21 Drawing Figures

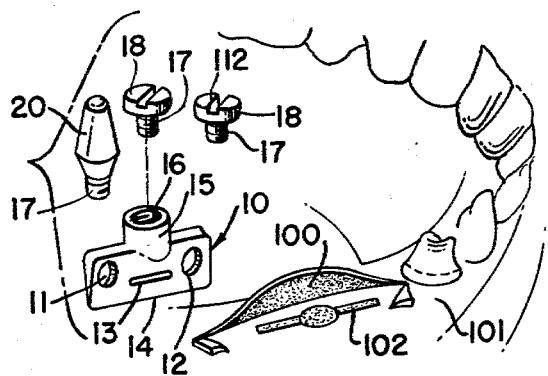
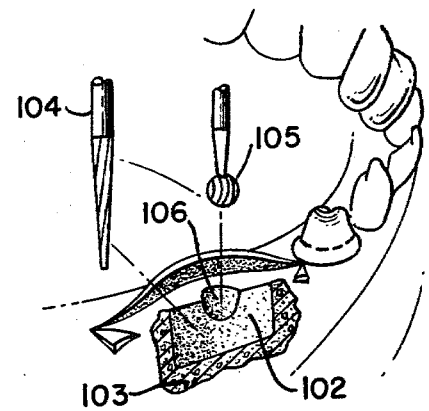
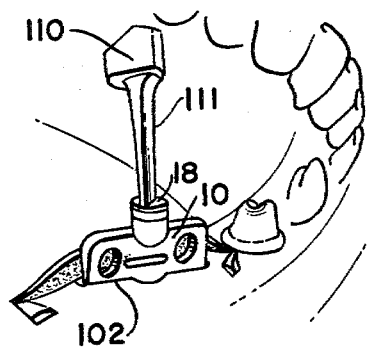
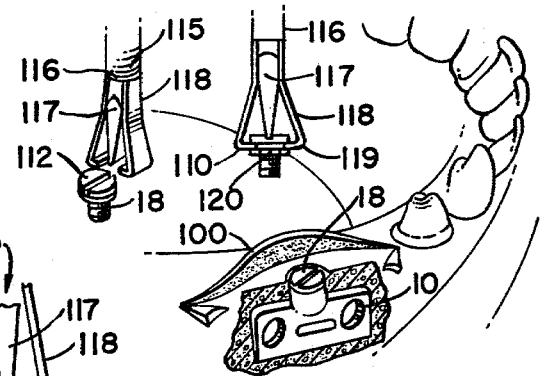
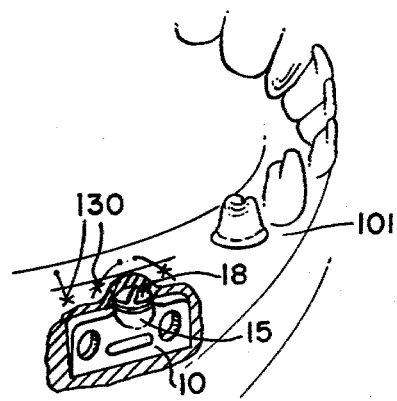
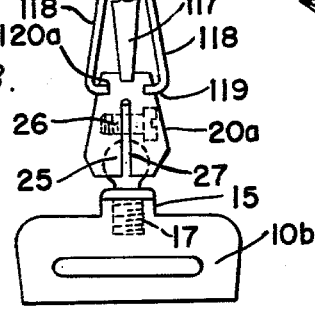
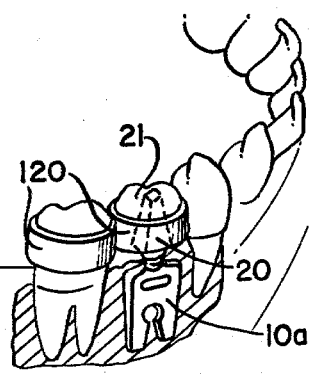
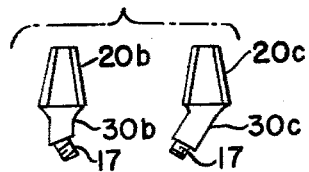

SUBMERGED FUNCTIONAL IMPLANT AND METHOD

RELATED APPLICATIONS

This application is a continuation of Ser. No. 819,119 filed July 26, 1977, which in turn is a continuation of Ser. No. 559,226 filed March 17, 1975, both now abandoned.

The invention relates to what are known in the art as dental implants and more particularly to a dental implant, which I chose to call a "SUBMERGED FUNCTIONAL IMPLANT", sometimes referred to herein as a SF implant. The invention also relates to a method of applying such SF implants and to tools for use in connection with such implants.

Dental implants of various designs are now well known in the art and in general are of two basic types:

(1) The post type which may be either rectangular or circular in cross-section as shown for example in FIGS. 1-4 and 10-12 inclusive, of the patent to Linkow and Edelman, U.S. Pat. No. 3,499,222, or (2) The blade type shown for example in my British Pats. Nos. 1,278,966 and 1,278,967, and in the following representative U.S. Pat. Nos. 3,465,441; 3,562,912; 3,623,226; 3,683,501; 3,690,005; 3,738,004; 3,738,008, and 3,798,771.

A blade type implant formed with apertures therein, as shown in some of the above patents is referred to herein as a "BLADE VENT" (R) the name being covered by Reg. T.M. No. 929,248.

Such dental implant, whether of the post type as shown in U.S. Pat. No. 3,499,222 or of the blade type, generally includes a main body portion adapted to be inserted in the jawbone of the patient and an integral neck and head portion adapted to support an artificial tooth and extending upwardly from the main body portion of the implant.

Various tools for inserting dental implants are shown for example in U.S. Pat. Nos. 3,562,912; 3,623,226, and 3,690,005.

Other prior art patents with which I am familiar include the following: U.S. Pat. Nos. 943,113; 2,609,604; 2,857,670; 3,548,499; 3,576,074; 3,577,853; 3,589,011, and 3,660,899. The above patents are representative only and are not all the patents in the field.

Certain defects have been found in standard implants and in the method of inserting such implants in the jaw as will be more fully setforth hereinafter in connection with the description of the preferred embodiment of the invention. The primary purpose of the present invention is to overcome such defects which are due in brief to the fact that the standard implant including an integral upstanding head portion, which projects above the gum is initially inserted into the jaw in such a manner as to permit foreign bodies to penetrate into the bone area and to permit movement to occur by lateral occulusion of opposing teeth. Such movement will loosen the one-piece implant.

In accordance with my invention the submerged functional implant is provided with a relatively short neck or collar portion, which is internally threaded to receive an externally threaded stem of a thin temporary cap or cover. It may also be externally threaded to receive an internally threaded stem. A suitable groove or opening is formed in the gum and jawbone by the use of standard drill and bar apparatus. The groove is of sufficient depth to completely enclose the implant including the cap, which is thereafter covered by the gum and the bone is allowed to penetrate any openings in the implant to cover the shoulders and horizontal walls of the collar. Subsequently, after a period ranging from several weeks to several months and after suitable testing to see if bone growth is optimal, the gum is again easily penetrated and the temporary cap removed, after which it is replaced by a head which projects above the jaw to which head an artificial tooth is applied above the jaw as is well known in the art. Various tools are employed in preparing the incision and applying the temporary caps and permanent head to the neck of the implant. Standard drills and/or pre-sized drills and burs may be employed in preparing the groove and special tools may be employed in preparing the groove and special tools may be employed for handing the cap and head.

The invention will be more reaily understood by reference to the accompanying drawing and the following detailed description which are intended as illustrative only and not as limiting the invention to the exact details as set forth in the drawing:

FIG. 1 is a diagramatic view showing a lower jaw with teeth projecting upwardly therefrom, and with an opening or incision shown formed in the jaw for reception of a submerged functional implant, which implant is shown externally of the groove in perspective together with temporary caps and a permanent tooth receiving head portion for the implant;

FIG. 2 is a view similar to FIG. 1, but showing the grooved portion of the jaw in section and also showing a conventional drill and bur for forming the opening;

FIG. 3 is a view similar to FIGS. 1 and 2 but showing the implant being inserted and a special tool having a flexible blade for use in contacting the implant in connection therewith;

FIG. 4 is a view similar to FIG. 2 but showing the capped implant in place in the groove and also showing special tools for handling the temporary caps for the implant;

FIG. 5 is a view similar to FIG. 4 but showing the capped implant submerged beneath the surface of the gum;

FIG. 6 is a view similar to FIG. 5 but showing the temporary cap replaced by a tooth receiving head which projects upwardly beyond the surface of the gum;

FIG. 7 is a perspective view of the lower jaw of a patient showing a modified implant and head with applied prosthesis and orthodonic bands;

FIG. 8 is an elevational view of another modified implant with a universal head mount and of a head applying tool partially shown;

FIG. 9 is an elevational view of a pair of angularly arranged implant heads.

Figure 10:
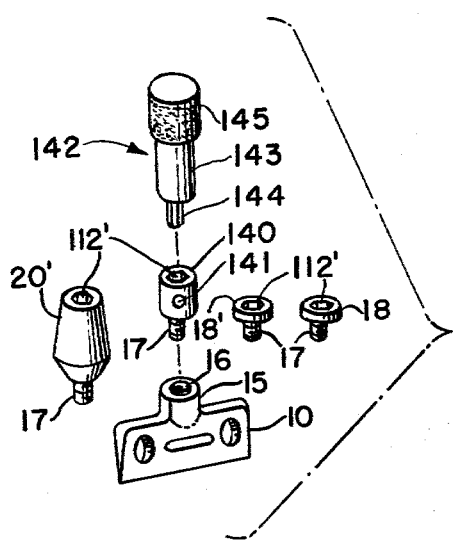
FIG. 10 is a diagramatic view corresponding to FIG. 1, showing a submerged functional implant together with a modified set of separate attachments which are selectively used in combination with the implant and a hexagonal headed screw driver for use in assembling and dissembling the heads and implant.

A standard "BLADE VENT" (R) or implant is designed to be inserted so that the so-called neck and post or head portion are integrally attached to the main body or insert portion of the implant. Because of this factor an opening is present between the oral cavity and the underlying bone area in which the implant is inserted. It is thus a possible route for entrance of micro organisms, epithelium, saliva or other foreign bodies to penetrate into the bone area causing a failure of the implant. The submerged functional implant is designed and inserted to avoid this possible contamination of subsequent rejection of the implant. The submerged functional implant also plays a significant role in correcting failures of other implants of either the "BLADE VENT" (R) type or the post or cylindrical type. Because of its unique design where a "BLADE VENT" (R) has failed the area can be curetted and the body portion of the submerged functional implant can be placed in that same area and sutured over so that bone repair will envelope the body of the implant. In the event a post or cylindrical type implant fails the necessary curetting and bone preparation for insertion can be done and the same procedure carried out using a post or cylindrical type submerged functional implant to replace the previously unsuccessful implant. Thus the submerged functional implant can be of great service to maintain the restoration prepared for the patient on a previous implant which failed, thus avoiding extra expenditures of time and cost factors. The submerged functional implant is the most successful approach to a free standing unsupported single tooth implant. By inserting the root portion, i.e., the insert portion of the SF implant, and allowing maximum calcification and deposition of bone over the shoulder portion and through the openings or concavity design, resistance to lateral displacement and movement can be overcome. After maximum deposition of bone determined by probings and x-ray findings, the head member can be inserted with minimal intervention on the part of the doctor. Thus the patient is assured of a predictive result unobtainable with any previous design.

PREFERRED EMBODIMENT

The SF implant is made so that the separate head member is provided with a male threaded stem at the apical or distal end of the head member. The body of the SF implant is made with a hollow collar or neck portion and a female thread to receive the threaded stem of the head member. The top of the collar may be located within the range from below the shoulder to an undertermined number of mm. above the superior portion or shoulder portion of the body of the implant. In average use the collar would be approximately 1½ mm. in height. Thus the collar in the method of insertion is implanted so its uppermost portion is approximately ½ to 1 mm. below the height of the alveolar crest of bone. (See FIG. 4 of the drawing). A lid or lids of various heights are made with grooves, flats or openings to receive a special screwdriver type instrument. The lid of choice is inserted into the collar portion so that it is at the same level as above or below the bone crest. (See FIG. 1 for various lids, and FIGS. 4 and 5 for positioning of the lid in bone and its relationship to the implant). In addition, an inserting cap (FIG. 1) of undetermined height is fabricated to protect the internal thread line and to allow an adjunctive means of inserting the SF implant as well as the slots which are fabricated in the shoulder portion of the SF implant to aid in insertion.

So-called lids may be made in several diameters and thickness in the event that it is desired to place a lid of lesser thickness to allow bone and tissue to embed or cover up to the superior portion of the lid at the sametime the shoulder portion or superior portion of the body and the body of the collar is being covered with bone and tissue.

The inserting cap varies from the head so far that insertion is expedited and protection is provided for the collar portion as needed. Thus we have both closing lids to prevent invagination of epithelium into the collar during the bone calcification and an inserting cap of a similar but modified design to allow inserting and protection of the collar. The inserting cap is removed at the initial insertion time and replaced by a covering lid which is allowed to remain until maximum bone deposition is achieved. They are then removed and replaced with a head member. The head members can be made in various designs. One of the heads is made with a base that is made to fit the dimensions of the collar portion circumferentially, and has a thinner portion 1.2 mm. less or more, to allow it to be bent to conform to the necessary occulusal plane levels needed for biting. A bending part and a holding part to allow the inclination of this head may be added. Such heads can be made to be bent either mesial distally or buccal lingually. This unique approach has many advantages over previous methods of achieving this purpose. Also heads which are machined to various inclinations may be employed to achieve a similar purpose. As shown in FIG. 7 the SF implant may be used as a free standing implant following maximum bone deposition over the root portion and several weeks to several months of splinting with orthodontic bands to the head member thus allowing final formation of the sulcus around the neck of the implant. With previous implants this could not be achieved either because of configuration or bulk or design. The SF implant qualifies with all necessary requirements.

A preferred technique for inserting a SF implant comprises forming a groove of the depth or approximately to the depth of the body of the SF implant including the height of the collar and the lid in the proper bone area of the ridge. A tapered helical bur and a round bur may be used to prepare the necessary groove and cylindrical portion of the preparation and the body of the SF implant or a tryin is then inserted for positioning and determination. For the use of a tryin see my U.S. Pat. No. 3,623,322 dated Nov. 30, 1972. A suitable retaining instrument may be used to insert the closing lid and the entire body, collar and closing lid are sutured over with the mucosal which has been incised originally. The inserting cap is used in a manner depicted in FIG. 3, to be an adjunctive aid in insertion. The patient's implant site is allowed to recalcify dependent upon the findings determined with probing and x-rays at different invervals. Thus the body of the implant with the head member removed and with the collar and female thread and closing lid embedded with the body, becomes surrounded and embedded by bone which in turn is covered by epithelium or tissue. At a desirable time an incision or trephine opening is made to expose the closing lid which closes the collar surmounting the body of the implant. The lid is then removed and the head member is engaged into the threaded portion of the collar and then allowed to be placed into function on a completely stabilized root portion of the implant, thus resisting opposing eccentric and protrusive tooth movement in occulusion (FIG. 6). The advantage of this method would be manifold. One advantage would be that the root body of the implant would be completely accepted by the body with consequent encapsulation by bone connective tissue and overlying tissue. This allows an implant to be used as a free standing unsupported tooth (FIG. 7), unlike the previous types of implants where the neck and body protrude into the oral cavity until accepted or rejected by the body. Thus the forces of mastication as well as pressures of other types engendered by cheeks, tongue or finger, or food movements, can result in a one piece implant becoming mobile with subsequent failure. The submerged functional implant completely allows the avoidance of pressures of the above type upon insertion and covering of the body root portion of an implant. In the event the SF implant is to be used as an abutment for a bridge the implantation of the root body as described above can be a determinant as to whether it is successful or will be a failure. This determination allows the doctor to decide whether to proceed with the cost and time consuming preparation of the bridge or whether a new procedure should be effected.

The technique for inserting the functionally submerged implant is as follows: An implant is made from various standard or custom designs to fit a particular bone site in length, depth and width, allowing for submergence of the root body and collar portion from 0 to any number of mm's. available below the alveolar crest. In some instances, it may be desired to allow the collar to protrude above the alveolar crest but covered with mucosa. In either case the following technique allows for the implant to be properly placed.

An incision of the overlying mucosa is done in a manner to expose the underlying bone so that the grooving for the body of the implant can be done with a drill preferably sized to or slightly narrower than the main body of the root section is drilled into bone to a width buccal-lingually narrower or wider than the body thickness of the implant. In the area where the collar portion will be located a presized bur is used to form an opening to receive the collar in its circumference and desired length (See FIGS. 1, 2, 3, 4 and 5). Thus the collar and body can be inserted into a close fitting preparation in a similar manner to standard type implants without undue difficulty. The head member or inserting cap is removed with ease to prevent pressure and movement and the closing lid is then inserted into the collar and the overlying tissue is sutured to prevent contamination and to allow healing to take place uneventfully (FIG. 5). The head member can be made in one piece or can be made with a ball arrangement so that the head may be positioned to parallel approximately abutment teeth or opposing teeth (FIG. 8). Various designs of implants either flat or round can be utilized with the ball neck head arrangement.

Referring more particularly to the Drawings FIGS. 1 to 7 inclusive, are diagramatic in character and are intended to illustrate successive steps in the implant procedure utilizing my improved submerged functional implant and showing a blade type implant together with tools for use at various stages.

A preferred form of submerged implant is generally designed by the reference numeral 10, and is shown as of the sharpened blade type having apertures 11, 12 and 13 therein to permit bone growth to penetrate after the implant is inserted in the jaw of the patient, thus permanently securing the insert in the jaw.

The lower edge 14 of the blade is shown as sharpened to facilitate entry into the jaw though such sharpening is not essential where a tryin as set forth in my U.S. Pat. No. 3,623,222 is employed. Other forms of dental implant may be employed instead of the blade type herein shown as will be apparent to those skilled in the art.

In accordance with my invention, the implant 10 is provided with a relatively short or shallow collar or neck portion 15, which, together with the blade portion is adapted to be completely enclosed within the recess groove or opening in the jaw as is best illustrated in FIGS. 6 and 5 of the drawings.

As shown the neck 15 is hollow and is internally threaded at 16, in order to receive the threaded stems 17 of suitable temporary caps 18, 18, which, if desired, may be of various diameters and thickness as may be required for different circumstances. The dentist or surgeon in charge will be supplied with such caps. In addition to the temporary caps 18, a permanent head 20 is provided, a portion of which, when the implant 10 is finally positioned as shown in FIG. 6, projects upwardly from the gum and is adapted to receive an artificial tooth 21 thereon as illustrated in FIG. 7, in connection with a submerged implant 10a of slightly different design from the preferred form 10 shown in FIGS. 1—6 inclusive.

As best shown in FIG. I the head 20 is provided with a threaded stem 17 corresponding with the stems of temporary cap 18, such stem 17 being adapted to fit in the threaded neck 15 of the submerged implant 10.

As will be apparent, various forms of the implant may be employed which may be of the post type or of the blade type, the latter being either sharpened or unsharpened and preferably being apertured. Also temporary caps of various sizes, diameters and thicknesses varying according to the requirements of the particular case may be employed; also the heads to which the artificial teeth are to be applied may be of different designs as illustrated, for example in 20a, (FIG. 8) and 20b and 20c in (FIG. 9).

Thus in FIG. 8 the implant blade 10b is provided with a shallow hollow neck 15 internally threaded to receive the threaded stem 17 of one of the temporary caps 18 shown in FIG. 1, or to receive the threaded stem 17 of a ball shaped member 25 adapted to rotatably receive a recessed artificial tooth retaining head 20a which may be rotated in all directions by reason of the universal ball joint 25 and may be secured in an adjusted position by means of the transverse screw 26, the head 20a being partially slotted as indicated at 27 and being formed of flexible material to permit the two portions of the head separated by slot 27 to be fitted on the ball portion 25 and thereafter to be tightened against the ball portion by means of the screw 26.

In FIG. 9 the artificial tooth retaining heads 20b and 20c are provided with shank portions 30b and 30c shown extended at angles to the respective head portions 20b and 20c and each provided with a threaded stem portion 17 adapted to fit the threaded neck 15 of the submerged implant 10 (FIG. 1).

The method of operation has been generally described but will now be further described with particular reference to the figures of the drawing.

Referring first to FIGS. 1 and 2, a thin external skin portion 100 of the gum 101 is partially cut away and folded back as indicated in the drawings. An elongated incision or groove 102 is formed in the jaw extending into the jawbone 103, as indicated in FIG. 2 of the size and shape to receive and fully enclose a submerged implant 10. The incision 102 may be formed by means of a conventional tapered drill 104 (FIG. 2), and a suitable bur 105 may be employed to enlarge the recess 102 at its center portion as indicated at 106 to receive the stem 15 of the implant 10. Thereafter, the implant including the neck or collar 15, to which a temporary cap 18 is applied is inserted in the groove 102 as indicated in FIGS. 3 and 4. A suitable tool 110 may be employed having a flexible blade portion 111 to permit bending at a suitable angle as may be required in applying the implant to the jaw of the patient. The end of the flexible blade 111 is flat and shaped to fit a transverse groove 112, formed in the temporary caps 18. The flexible blade 111 may be of any suitable material such as rubber, flexible metal or the like.

FIG. 4 shows a modified tool 115 for handling the caps 18. This tool includes a handle portion 116 and a blade portion 117 which may be similar to the flexible blade 111 of the tool 110. The tool 115 also includes a pair of flexible grasping fingers 118, 118 each including a grasping portion 119 adapted to engage a circumferential groove 120 formed in the temporary cap members 18. The spring fingers 118 are biased inwardly to cause the grasper portions 119 to retain the screw caps 18. The tool 113 may also be used to grasp and apply the head 20a shown in FIG. 8, which may be formed with a groove 120a to receive the graspers 119.

After the submerged implant 10 has been fully inserted in the groove 102 with the neck portion 15 and cap 18 lying below the surface of the gum the skin portion 100 is folded down to completely enclose the submerged implant and cap 18 as indicated in FIG. 5. Thereafter sutures 130 are applied to hold the skin in place.

After suitable time, as determined by the doctor or surgeon in charge of the operation, the skin portion 100 is again opened by exposing the cap 15 which is then removed by use of a suitable tool, whereupon a tooth receiving head 20 is applied to the submerged blade 10 as indicated in FIG. 6. The head 20 projects above the surface of the gum and is adapted to receive an artificial tooth 21 (FIG. 7). This figure also shows the use of orthodontic bands 120 previously referred to.

It will be apparent that various types of inserts may be employed and also various forms of heads may be employed as for example the universally mounted head 20a shown in FIG. 8, or the angularly arranged heads 20b and 20c shown in FIG. 9.

In FIG. 10 are shown a modified permanent head 20', a pair of modified temporary heads or caps 18', 18' of different sizes and an inserting and removing head 140, each having a threaded stem 17 for threaded engagement with a short hollow internally threaded collar portion 15 of a submerged functional implant such as the blade type implant 10 previously described. The temporary caps 18' and the permanent head 20' are like the corresponding caps 18 and permanent head 20 illustrated in FIG. 10, with the exception that a hexagonal socket 112' is provided in the top of the caps 18' and head 20' instead of the slots 112 which are provided in the caps 18 and head 20.

The hexagonal sockets 112' are adapted to receive therein the hexagonal shank 144 of a special hex-screw driver 142, or Allen wrench, for screwing the threaded stems 17 of the caps 18' and permanent head 20' into the threaded bore 16 in the neck portion 15 of the implant 10. The screw driver 142 has a cylindrical body 143, a hexagonal shank 144 and an enlarged cylindrical, knurled handle portion 145 at the end of the body opposite the shank 144. FIG. 10 further shows a cylindrical, implant inserting and removing head 140 with which has a threaded shank 17 for threaded engagement with the threaded bore 16 of the implant 10 and a transverse bore 141 extending through the cylindrical head to receive the cylindrical, right angle of an implant inserting and removing tool 146 illustrated in FIG. 11. The implant inserting and removing head 140 has a hexagonal socket 112' in its top end to receive the shank of the hex-screw driver 142.

Figure 11:
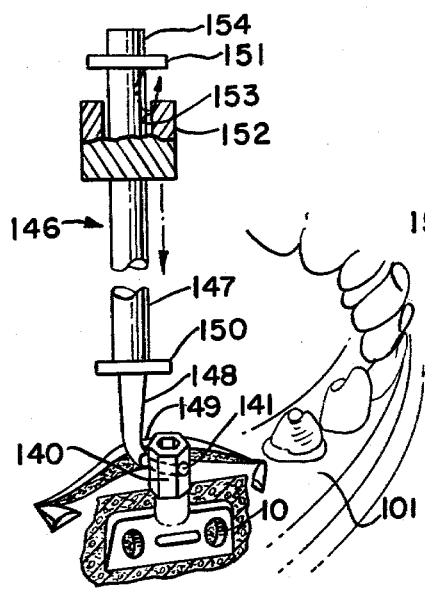
FIG. 11 is a diagramatic view of a submerged functional implant embedded in the jaw with an inserting and removing head applied to the implant and an inserting and removing tool in position for inserting or removing the implant.

FIG. 11 is like FIG. 4, in that it shows an implant 10 after it has been implanted in the jaw. However, the inserting and removing head 140 has been substituted for the slotted cap 18 which is shown in FIG. 4. The use of the head 140 instead of the cap 18 while inserting the implant 10 and/or removing same, if necessary, permits more positive application of implanting and removing forces by the implanting and removing tool 146 without danger of the tool slipping from the head than is possible with the slotted cap 18 and the tool 110. The implanting and removing tool 146 comprises a cylindrical body 147 having enlarged cylindrical anvils 150 and 151 at its opposite ends, a cylindrical hammer sleeve 152 freely slidable over the cylindrical body between the anvils and a tapered shank 148, extending axially from the cylindrical body beneath the anvil 150 and a right angle cylindrical projection 149 at the reduced end of the tapered shank 148. The diameter of the right angle projection 149 is slightly less than the diameter of the bore 141 in the inserting and removing head 140 so that it may fit closely within the bore without excess play. The anvil 150 is preferably integral with the cylindrical body 147, while the anvil 151 is removable to permit the body 147 to be inserted through the axial bore 153 of the hammer sleeve 152. The anvil 151 is removably retained at the end of the body 147 by a knurled cap 154 which has a threaded stem (not shown) adapted to extend through an axial bore in the anvil 151 into an interiorly threaded bore at the end of the cylindrical body 147.

When the cylindrical right angle projection 149 of the inserting and removing tool 146 is engaged in the transverse bore 141 of the inserting and removing head 140 with the axis of the cylindrical body 147 parallel with the axis of the head 140, as shown in FIG. 11, impact forces can be applied to the inserting and removing head by sliding the hammer sleeve 152 along the body 147 until it strikes one of the anvils 150 and 151. By striking the anvil 150 inserting forces are transmitted through the inserting and removing head to seat the implant 10 in a preformed groove in the jaw. If it is desired to remove the implant 10 from the jaw, the hammer 152 is reciprocated along the body 147 to repeatedly strike the anvil 151. The repeated outwardly directed impact force against the anvil 151 will unseat the implant 10 from the jaw.

Figure 12:
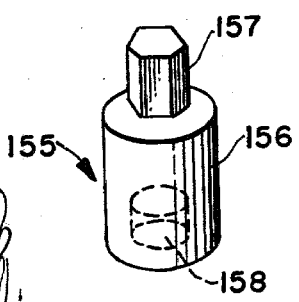
FIG. 12 is an enlarged perspective view of a final seating head for use with an inserting instrument for engaging over the top of the inserting and removing head.
Figure 13:
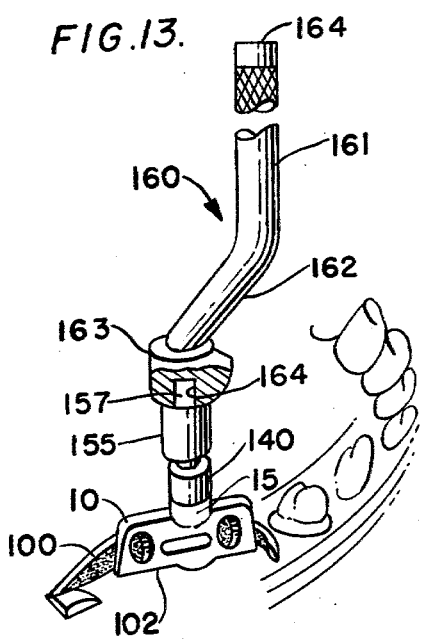
FIG. 13 is a view similar to FIG. 3 showing an implant seated in a groove formed in the jaw, an inserting and removing head attached to the implant, a final seating head in position to engage the top of the inserting and removing head and an inserting tool in position to finally seat the implant.

FIG. 12 is an enlarged view of a final seating head 155 adapted to be used in combination with appliance 160 for inserting dental implants in the manner illustrated in FIG. 13. The final seating head 155 includes a cylindrical body portion 156 having at one end an axially extending socket 158, and at its other end an axially extending hexagonal stud portion. The socket 158 is of slightly larger diameter than the diameter of the inserting and removing head 140, so that the final seating head may be fitted over top of the inserting and removing head with the socket 158 fitted closely thereon. The hexagonal stud portion 157 is of a size to fit within the hexagonal socket 164 provided at one end of the inserting appliance 160. The inserting appliance 160 is disclosed in U.S. Pat. No. 3,562,912 issued to Alfred E. Edelman on Feb. 16, 1971. It includes a handle 161 having at one end an enlarged offset end portion 163, which is connected to a straight handle portion 164 by an angled handle portion 162. The offset end portion 163 has an open-ended recess 164 of hexagonal cross section which is adapted to receive therein the hexagonal stud portion of the final seating head. In use the handle portion 164 of the inserting appliance 160 is held outside of a patient's mouth with the offset portion 163 positioned inside the mouth and engaged over the final seating head in the manner shown in FIG. 13. The open-ended recess 158 of the final seating head 155 fits closely over the removing and inserting head 140 which is screwed into the threaded bore 16 of the implant 10. A downward force applied to the handle of the inserting appliance 160 will force the implant 10 into the groove 102.

After the implant 10 has been driven into the desired position using the inserting appliance 160, final setting head 155 and inserting and removing head 140, the inserting and removing head 155 is unscrewed from the implant 10 using the hexscrew driver 142, and one of the temporary caps 18' of appropriate height is screwed into threaded bore 16 of the implant 10 to close same. The gum portion 100 will then be layered back over the implant and sutured closed in the manner illustrated in FIG. 5. The process for removing the temporary cap 18' after bone has closed around the implant 10 and applying a permanent head to the implant is the same as had been described with respect to FIGS. 1-6.

Figure 14:
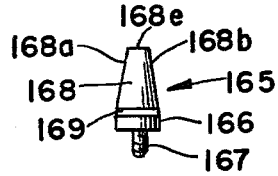
FIG. 14 is a front elevational view of an angulation head for the functional submerged implant shown in FIG. 10.
Figure 15:
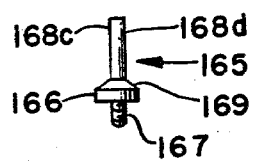
FIG. 15 is a side elevational view of the angulation head shown in FIG. 14.

FIGS. 14 and 15 show an angulation head 165 to be used in lieu of the heads 20,20', 20a, 20b, and 20c previously described. The angulation head 165 comprises a cylindrical cap portion 166, an exteriorly threaded stem 167, and a thin flat upstanding head portion 168. The cap portion 166 is of substantially the same diameter as the outside diameter of the collar portion 15 of the implant 10, and the exteriorly threaded stem 167 is of a size to threadedly engage the threaded bore 16 of the implant. The head portion 168 has parallel opposite front and back faces 168c and 168d, and sloping side surfaces 168a and 168b which slope inwardly from the juncture of the head with the cap portion 166 toward a flat top 168e which is parallel to the cap portion 166. The top of the cap portion 166 is beveled inwardly at 169 toward the head portion 166. The angulation head 165 is made of a bendable material so that the head portion may be bent laterally relative to the broad faces 168c and 168d using a bending tool 170 illustrated in FIG. 16.

Figure 16:
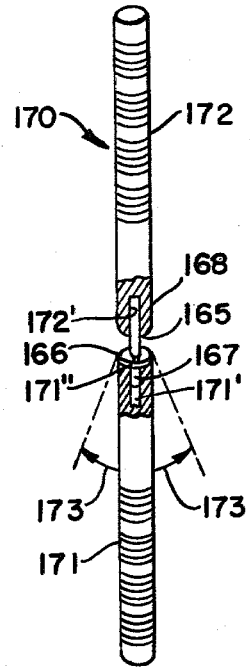
FIG. 16 is a partial sectional view of a bending tool for the angulation head shown in FIGS. 14 and 15.

The bending tool 170 includes a cylindrical threaded holder 171 and a cylindrical bending shaft 172. The threaded holder 171 has an axial bore 171' which extends inwardly from one end and engages the threaded shank 167 of the angulation head 165 therein with the cap portion seated on the flat end face 171'' of the threaded holder. The bending shaft 172 had an axially extending slot 172' at one end which is of a size and shape to receive the head portion 168 of the angulation head therein. With the angulation head 165 engaged by the threaded holder and the bending shaft as shown in FIG. 16, the head portion may be bent laterally relative to the cap portion 166 by grasping the threaded holder with one hand and the bending shaft with the other hand and applying a bending force.

Figure 17:
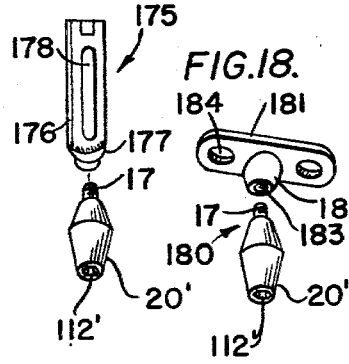
FIG. 17 is an exploded perspective view of an anterior replacement implant.

While the invention has been described so far particularly with respect to the blade type implant 10, it is to be understood that the invention is applicable to various other type implants such as for example, those illustrated in FIGS. 17-20. FIG. 17 illustrates an anterior replacement implant generally designated by the reference numberal 175. It comprises a narrow elongated flat blade portion 176 and a collar portion at/one/in which is located or interiorly threaded axial bore for receiving the threaded shank of a permanent head 20', or any one of the heads or caps illustrated in FIGS. 1 and 10, which are adapted for use with the blade implant 10. The blade portion 176 has a longitudinal groove 178 extending centrally on each side thereof into which bone may grow and interlock with the implant to hold it firmly implanted. In use the implant 175 is implanted in a prepared opening in the jaw in a like manner to the implanting of the implant 10, as had been described.

Figure 18:
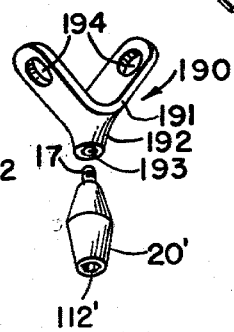
FIG. 18 is an exploded perspective view of a T implant.

FIG. 18 shows a T implant 180 comprising a separate head 20' and in insert portion including a flat planar base portion 181 and a hollow frusto conical neck portion 182 integral with the base portion and projecting perpendicularly from the center thereon. The neck portion 182 has an internally threaded bore for receiving the threaded stem 117 of the separate head 20'. Holes 184 are provided in the jaw portion 181 on opposite side of the collar to receive bone growth therein for interlocking with the base portion 181.

Figures 19, 20:
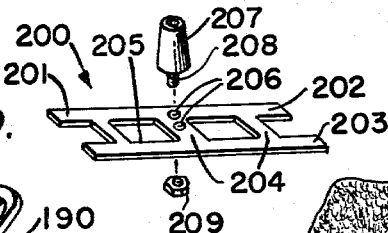
FIG. 19 is an exploded perspective view of a Y implant.
FIG. 20 is an exploded perspective view of a subosseous implant.
Figure 21:
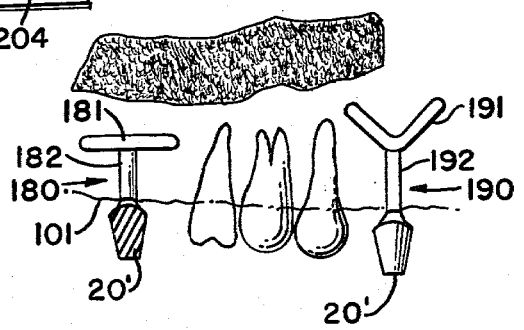
FIG. 21 is a sectional view through an upper jaw showing the T implant and Y implant embedded in the jaw.

FIG. 19 shows a Y implant 190 comprising a separate head 20' and an insert portion including a V-shaped base portion 191 and a short hollow neck portion 192 formed integrally with the base at the apex of said V. The neck portion 192 has an integrally threaded bore 193 for receiving the threaded stem 17 of the separate head 20'. Holes 194, 194 are provided in opposite legs of the V-shaped base to receive bone growth therein.

The insert portions of both the T and Y implants are of such shape as to require the formation of slots in the jaw of comparable shape, the slots being formed by first incising the mucosa laterally of the alveolar crest and drilling into the jaw to form slots of the appropriate shape corresponding to the shape of the base portion. The base portions 181 and 191 are then inserted laterally into the slots prepared in the jaw, whereupon the mucosa is sutured closed. Incisions are made in the mucosa covering the alveolar crest in alignment with the neck portions 182 and 192 to expose the threaded bores 183 and 193 respectively. Temporary caps such as the caps 18' are then threaded on the necks 182 and 192 to close same and the mucosa over the alveolar crest as sutered closed. After a suitable period of time has elapsed to permit the mucosa to heal and the base to grow around the implants 180 and 190, incisions are again made in the mucosa to expose the neck portions 182 and 192, whereupon the temporary caps 18' are removed and permanent head members 20' are implanted.

FIG. 20 shows a sub-osseous implant 200 comprising a thin, substantially flat, planar insert portion 201 adapted to be embedded in a shallow groove of a shape corresponding to the insert portion 201 formed across the alveolar crest of the patient's jaw. The insert portion 201 is generally ladder shaped having spaced parallel side rails 202 and 203 and plural transverse connecting bars 204 which define plural openings 205. Several internally threaded bores 206 are provided along the central cross bar 204; they extend through the thickness of the insert portion and are adapted to receive the threaded stem 208 of a separate elongated head portion 207 in a selected one of the bores. The head 207 when threaded into a selected one of the bores 206, extends outwardly with its longitudinal axis perpendicular to the insert portion 201. Preferably the threaded stem 208 is longer than the thickness of the insert portion so that the stem 208 when fully threaded into one of the bores 206 will extend beyond the insert portion where it is fastened by a threaded nut 209 on the underside of the insert portion 201. The nut 209 may be soldered or otherwise secured to the underside of the insert portion 201 in axial alignment with one of the bores 206. The ends of the rails 202 and 203 are preferably sharpened so that when the ends of the rails beyond the end cross bars 204 are bent downwardly, generally perpendicular to the body of the insert portion, the down turned ends may be driven into the alveolar crest to more firmly hold the sub-osseous implant in place.

When implanting the sub-osseous implant 200 the mucosa overlying the alveolar crest where implanatation of the implant 200 is desired is incised and laid back. A shallow groove is formed in the alveolar crest of a depth approximately equal to the thickness of the insert portion 201 and of a shape and size similar to the exterior size and shape of the insert portion. After forming the groove, the insert portion is placed in the groove and its bentover ends are driven into the bone at the bottom of the groove. The mucosa is then placed back over the groove and insert and sutured closed. After a suitable period of time to permit bone to grow through the openings in the insert 201 to immobilize the insert portion, an opening is incised in the gum over the bore 206, which is selected for attachment of the head 207 and the head 207 is threaded into the bore and nut 209.

Some posts which are used for final restoration are simular to the post No. 20 in FIG. 6, or are conical in shape, or are thin bodied extensions which are attached to a threaded round base by a radius which does not allow undercuts so that impressions can be removed. Undercuts may be desired for various retentive reasons and may be so designed on posts to retain either fixed or removable restorations. The posts may be so designed as to have an aperture running centrally through two parallel walls to engage a tract that is curved to engage a similar designed head or series of heads attached to other implants, either SF or of another type. The posts may also be designed with circular nonundercut surfaces to engage a track or restoration with friction fit. Posts may be designed to various manners for the purpose of retaining restorations or tracklike bars or supporting structures for the purpose of attaching a removable or fixed prosthesis. This will provide a more economical method of restoration to allow patient use and acceptance.

The SF implant has application with a uniquely designed post or receptacle to allow it to be placed in the ascending portion of the body of the mandible, thus with one of each in each of the mandible ramil, and one, two or more SF type placed advantageously in the mandible and allowed to become embedded in bone. When bone has embedded or enveloped the body and collar portion of the SF implants a framework can be placed on the various designed heads or receptables of the SF implant. This method is a vast improvement over previous methods, inasmuch as the acceptance of the human body can first be determined of the substructure or root forms, an impression can be taken with the respective posts or receptacles in place, and a frame or connecting structure can be either bent or cast previous to the patient's return to the office. This method also allows much more precision restorative bars or rails, and eliminates undue bone pressure and the need for an immediate replacement of the previous methods required. This method also allows the dentist precise selection and lodgement of the SF implant to be the abutment in each ramus and diminishes or curtails completely the possibility of impinging upon the mandibular canal, as it makes its egrees into the skull. Thus this method and embodiment of configuration is superior in all respects from a viewpoint of patient well being and economics to the time factor and ease of insertion plus the predictability factors enjoyed by the dentist. The SF implant differs from previous implants in that it embodies a combination of flat and ovoid configurations and plane surfaces to encourage physiological and mechanical retention eliminating undue trauma to the patients, and a factor of economics because its acceptance is predictive within several weeks. This factor is not available in any previous implant design.

What is claimed:

1. A submerged dental implant comprising a nonrotatable insert portion including an enlarged permanent body portion and a short hollow internally threaded neck portion of relatively small cross-section adapted to receive the threaded stem of a thin removable temporary cap member or a similarly threaded stem of an artificial tooth receiving head, said insert portion including an applied cap being adapted to be wholly submerged in a recess of the patient's jaw and thereafter covered by surface skin of the jaw and after a considerable period of time the surface skin of the gum and the temporary cap of the said submerged implant may be removed, said submerged implant neck portion being then adapted to receive an artificial tooth receiving head member which projects above the surface of the gum to receive an artificial tooth, said tooth receiving head member having a stem fitting the neck of the insert and a universal joint including a ball member, and a socket portion fitting over the ball member, said socket portion being externally shaped to receive an artificial tooth, said socket portion comprising a pair of flexible side portions, partially separated by a split and adjustable means for holding said flexible portions in engagement with the ball member of the joint.

* * * * *